United States Patent [19]

Gradeff et al.

[11] Patent Number: 4,489,000
[45] Date of Patent: Dec. 18, 1984

[54] PROCESS FOR THE PREPARATION OF CERIC ALKOXIDES

[75] Inventors: Peter S. Gradeff, Pottersville; Fred G. Schreiber, Highland Park, both of N.J.

[73] Assignee: Rhone-Poulenc Inc., New Brunswick, N.J.

[21] Appl. No.: 521,787

[22] Filed: Aug. 9, 1983

[51] Int. Cl.$^3$ .................................................. C07F 5/00
[52] U.S. Cl. .................................................... 260/429.2
[58] Field of Search ..................................... 260/429.2

[56] References Cited

U.S. PATENT DOCUMENTS 3,631,081 12/1971 Huggins et al. ............. 260/429.2 X
3,975,416 8/1976 Mazdiyasni et al. ............. 260/429.2

Primary Examiner—Leland A. Sebastian

[57] ABSTRACT

A process is provided for preparing ceric alkoxides, which comprises reacting ceric ammonium nitrate with an alcohol, including a lower aliphatic alcohol, under anhydrous conditions in the presence of an anhydrous base at a temperature within the range from about −30° C. to about 200° C. but preferably from 0° to about 150° C. until ceric alkoxide and the nitrate salt of the base are formed; ceric alkoxides of higher alcohols can be prepared by transetherification of the resulting ceric alkoxide with the higher alcohol, either simultaneously or sequentially, at a temperature within the range from about −30° C. to about 200° C., thereby displacing the lower aliphatic alcohol and forming the ceric alkoxide of the higher alcohol, while distilling off free lower aliphatic alcohol in the course of the transetherification, to drive it towards completion; the nitrates formed during the reaction can be separated from the reaction mixture and the alkoxides isolated pure or as complexes with the alcohol, or in some cases the alkoxides can be used without separation from the reaction mixture in the presence of the nitrates.

15 Claims, No Drawings

PROCESS FOR THE PREPARATION OF CERIC ALKOXIDES

Polyvalent metal alkoxides are an important class of versatile organometallic compounds that have many industrial uses. In some instances their uses parallel the metal carboxylates and other organometallic compounds, but they have advantages over such compounds because of their catalytic properties, ease of hydrolysis, solubility in organic solvents, and volatility. They have been used as paint additives, water repellents, adhesion promoters, mordants, sizing agents in enamel compositions, catalysts and also very importantly as intermediates in synthesis of other organic compounds.

There are four general preparative methods for metal alkoxides, all under anhydrous conditions, as follows:

A. By reaction of the corresponding alcohol and metal, such as the alkali metals, alkaline earth metals, and aluminum, with the assistance of an alkaline or acidic catalyst.

B. By reaction of the corresponding alcohol with the oxides and hydroxides of the metal, for instance NaOH or $Na_2O$, $V_2O_5$ and $MoO_3.2H_2O$.

C. By reaction of the corresponding alcohol and metal halide in the presence of an anhydrous base. A typical example is the preparation of $Th(OR)_4$ or $Zr(OR)_4$:

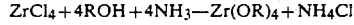

The reaction can be used for preparing alkoxides of titanium, hafnium, germanium, niobium, tantalum, aluminum and tin.

D. By transetherification of the metal alkoxides of lower alcohols, such as the methoxides, ethoxides or isopropoxides, with a higher alcohol.

Method A is exemplified for a number of yttrium, lanthanum and other lanthanide alkoxides by L. Brown and K. Mazdiyasni in *Inorganic Chemistry*, (1970) 2783. The reaction, previously thought to be useful only for the alkali metals, magnesium and aluminum, was extended by them to the synthesis of yttrium and all of the lanthanide isopropoxides. For the lower lanthanides, such as lanthanum, cerium, praesodymium and neodymium, a mixture of $HgCl_2$ and $Hg(C_2H_3O_2)_2$ or $HgI_2$ is used as a catalyst, to increase both the rate of reaction and percent yield. Generally, 5 g of metal turnings is reacted with about 300 ml of isopropyl alcohol at reflux temperature for about 24 hours and in the presence of a small amount of Hg salt catalyst. The yields are said to be 75% or better.

Most of the other examples in the literature of the preparation of alkoxides of lanthanides refer to the use of the corresponding metal halides. In some cases, a complex $LaCl_3.3ROH$ is preferred to the $LaCl_3$ (Misra et al, *Austr J Chem* 21 797 (1978) and Mehrotra and Batwara, *Inorganic Chem* 9 2505 (1970)).

An interesting variation of Method D is mentioned by Tripathi, Batwara, and Mehrotra *J.C.S.A.* 1967 991. Lower ytterbium alkoxides (such as the methoxide and ethoxide) were synthesized from ytterbium isopropoxide, by transetherification with methanol or ethanol. Owing to their sparing solubility, these alcohols were removed by precipitation as the reaction proceeded, driving the transetherification to completion.

In general, Methods A, B and C are only suited for preparation of the lower alkoxides, such as the methoxides, ethoxides and isopropoxides, since the reactivity of higher alcohols diminishes with increase in their molecular weights. The higher alkoxides are better prepared by Method D, which is a two-step process.

The only published method for preparing ceric alkoxides applied Method C to ceric chloride, Bradley et al, J.C.S. 1956 2260–64. Since cerium tetrachloride is unstable, the dipyridinium cerium hexachloride complex was Bradley et al's choice as starting material.

Cerium dioxide was first converted to ceric ammonium sulphate. Pure ceric hydroxide was precipitated from an aqueous solution of ceric ammonium sulphate and washed thoroughly. The freshly-prepared ceric hydroxide, suspended in absolute alcohol, was treated with anhydrous hydrogen chloride and then pyridine was added, which formed the insoluble dipyridinium cerium hexachloride complex $(Py)_2CeCl_6$. The complex was filtered, dried, and used for preparing the methoxide, ethoxide and isopropoxide directly, while the propyl, butyl, secondary butyl, neopentyl and n-pentyl alkoxides were made by alcohol interchange, i.e., transetherification, from the isopropoxide. The methoxide and ethoxide were also made by exchange from the isopropoxide.

In accordance with the present invention, a process is provided for preparing ceric alkoxides which comprises reacting ceric ammonium nitrate with an alcohol under anhydrous conditions in the presence of an anhydrous base at a temperature within the range from about $-30°$ C. to about 200° C., preferably from about 0° C. to about 150° C., until ceric alkoxide and the nitrate salt of the base are formed.

This process avoids the necessity described by Bradley et al of first preparing the ceric hydroxide from the ceric salt, in their case, ceric ammonium sulphate, and converting the hydroxide subsequently to the chloride, which needs to be stabilized as the pyridine complex. The process of the invention is direct and economical, and in addition utilizes ceric ammonium nitrate, a commercially available material that is relatively inexpensive.

Cerium alkoxides are thought to exist in the form of the alkoxide and as association complexes with free alcohol, and since these appear to be unstable, as decomposition products thereof. Mixtures of all of these are what are commonly referred to as "cerium alkoxide", and so the term is used herein in this commonly accepted sense.

The process proceeds with ease with the lower aliphatic alcohols having from one to five carbon atoms, for example, methanol, ethanol, propanol, isopropanol, butanol, isobutanol, sec-butanol, tert-butanol, pentanol, isopentanol, sec-pentanol, and tert-pentanol. If a ceric alkoxide of a higher aliphatic alcohol having at least six up to about twenty carbon atoms is desired, such as for example hexanol, heptanol, isoheptanol, octanol, isooctanol, 2-ethyl-hexanol, sec-octanol, tert-octanol, nonanol, isononanol, decanol, dodecanol, tetradecanol, octadecanol, hexadecanol, oleyl alcohol, and eicosyl alcohol; or a cycloaliphatic alcohol having from three to about twenty carbon atoms, such as for example cyclopropanol, cyclobutanol, cyclopentanol, cyclohexanol, cycloheptanol, cyclooctanol, cyclododecanol, tripropyl cyclohexanol, methyl cyclohexanol and methyl cycloheptanol; or an alkyl aromatic alcohol having from seven to about twenty carbon atoms, such as for example benzyl alcohol, phenethyl alcohol, phenpropyl alcohol, phenoctadecyl alcohol and naphthdecyl alcohol.

The higher alcohol can be incorporated directly in the reaction mixture together with a lower aliphatic alcohol having from one to five carbon atoms. The final reaction product is the ceric alkoxide of the higher alcohol, but it is believed that the lower alcohol expedites the reaction by first forming an alkoxide with the cerium, this alkoxide being converted by transetherification with the higher alcohol to the alkoxide of the higher alcohol.

The conversion is facilitated if the free lower aliphatic alcohol formed by displacement in the transetherification reaction is removed by distillation from the reaction mixture in the course of the reaction, thus aiding in driving the transetherification reaction towards completion. Thus, in this aspect of the invention, the higher alkoxide is produced in one step by a series of reactions that are carried on simultaneously in the same reaction mixture, without the need for separation of an intermediate lower alkoxide reaction product. The only requirement is that the alcohol used be stable to oxidation by the ceric ion in the course of the reaction.

The above-described reactions can be carried out in the presence of an excess of the alcohol, which if a higher alcohol can be a solvent for the corresponding alkoxide. Other inert solvents in addition to the reactant alcohol can also be used such as benzene, hexane and acetonitrile. If desired, the solvent can easily be separated from the reaction product by distillation at atmospheric or reduced pressure, following completion of the reaction.

The reaction proceeds under anhydrous conditions at a temperature within the range from about $-30°$ C. to about 200° C., preferably from about 0° C. to about 150° C., most preferably at room temperature, depending on the solvent system and base used.

The reaction proceeds in the presence of a suitable anhydrous base, such as ammonia, or an alkali metal alkoxide, desirably of the corresponding alcohol, so as to avoid contamination of the alkoxide reaction product with another alkoxide. A byproduct of the reaction is the corresponding ammonium or alkali metal nitrate salt.

Exemplary anhydrous bases include sodium methoxide, sodium ethoxide, potassium methoxide, potassium ethoxide, sodium isopropoxide, sodium isobutoxide, lithium methoxide and lithium ethoxide.

The reaction time is not critical. The reaction is continued until the desired alkoxide product is formed. This may take from ten minutes to several hours, but it is not necessary to carry the reaction beyond a five hour reaction time. Usually, reaction is complete within from one to three hours.

The reaction can proceed quite rapidly at room temperature, and if it does, it very likely will also proceed at temperatures well below room temperature, down to $-30°$ C., but there is no reason to incur the additional expense of cooling the reaction mixture. The upper limit on reaction temperature is imposed by the volatility of the reaction mixture or any component thereof, and their decomposition temperature. There is no reason to use a temperature above the boiling point of the reaction mixture at atmospheric pressure, but if the boiling temperature is too low, as, for example, in the case of methanol, a closed reaction vessel or pressurized system can be used. The reaction temperature need not exceed 200° C., taking the above factors into consideration.

The amount of anhydrous base is stoichiometric, since the function of the base cation, ammonia or alkali metal, is to take up nitrate from the ceric ammonium nitrate starting material. An excess can be used, but is unnecessary.

Similarly, the amount of alcohol is at least the stoichiometric amount required to react with the ceric ammonium nitrate, but higher amounts can also be used. Larger than stoichiometric amounts will be used, of course, when the alcohol is also to function as a solvent, according to the dilution of the reaction mixture required.

The reaction mixture contains the nitrate salt of the base cation, and this can be separated from the alkoxide during work-up. If this salt is less soluble in the reaction mixture than the alkoxide reaction product, it can be filtered off, and thereby separated from the reaction product. Alternatively, the reaction mixture can be taken up in an inert solvent such as benzene, toluene or hexane, preferably an inert solvent in which the alkoxide reaction product is soluble, and the nitrate or salt insoluble, whereupon the nitrate salt is filtered off or centifuged out.

In the cases of lower alcohols, the product as well as the nitrate are solids. In this case, filtration cannot of course separate the two; the alkoxide reaction product can be recovered and separated from the nitrate salt by extraction with a solvent for the alkoxide in which the nitrate salt is insoluble, using, for example, a Soxhlet apparatus. Alternatively, a solvent for the nitrate salt can be used in which the ceric alkoxide is insoluble. For example, ammonium nitrate is quite soluble in methanol, while ceric tetramethoxide is not, and so in this case ammonium nitrate can be separated by extraction with methanol. Sodium nitrate can also be separated in this way, although it is less soluble in methanol.

Depending on reaction and work-up conditions, the alkoxide can be isolated as associations with one or more molecules of alcohol that generally renders it more stable to hydrolytic decomposition. On the other hand, the alkoxide can be isolated in a partially hydrolyzed form suitable or desirable for certain applications.

For some applications the cerium alkoxides can be used in the form they exist in the reaction mixture at the end of the reaction, without actually isolating them from the reaction mixture, or separating them from the nitrates, which saves processing and handling costs.

The following Examples in the opinion of the inventors represent preferred embodiments of the invention:

EXAMPLE 1

Preparation of Ceric Tetrabenzyloxide from Ceric Ammonium Nitrate Sodium Methoxide in Methanol and stoichiometric amount of benzyl alcohol To a stirred solution of 16.50 g (0.0301 mole) ceric ammonium nitrate in 60.6 g methanol under argon to maintain anhydrous conditions during the reaction at room temperature was added 30.1 g (0.1810 mole) 25% anhydrous sodium methoxide solution. After the bright yellow mixture had been stirred for 15 minutes, 13.0 g (0.1202 mole) benzyl alcohol was added followed by 41.0 g toluene.

After 1 hour, methanol/toluene was distilled out until the mixture became too thick to stir. Fresh toluene was added, to keep the contents slurried, while heating until the boiling temperature reached 104° C.

The sodium nitrate was filtered off and washed with four portions of toluene. Weight of nitrate=15.3 g (theory 15.35). The dark brown filtrate was concentrated down under reduced pressure until no more liquid distilled.

The product, ceric tetrabenzyloxide, was a dark brown, runny oil, 17.9 g, theory=17.11 g. Residue analysis=30.01% ash, theory 30.27%; % C found 58.81, theory 59.14; % H found 5.23, theory 4.96.

EXAMPLE 2

Preparation of Ceric Tetramethoxide from Ceric Ammonium Nitrate, Ammonia, and Methanol Anhydrous ammonia gas (2.1 g) was added to a solution of ceric ammonium nitrate (16.46 g) in methanol (102.90 g) with vigorous stirring over 2.5 hours. The solids were filtered off, and washed four times with methanol. The residue after drying was 6.11 g of bright yellow solid, ceric tetramethoxide. The yellow filtrate was evaporated to dryness to give 15.42 g pale yellow solid, predominantly ammonium nitrate, with some ceric tetramethoxide responsible for the yellow color. The material balance on cerium was quantitative.

EXAMPLE 3

Preparation of Ceric Tetraoctoxide from Octyl Alcohol Sodium Methoxide and Methanol To a solution of 5.48 g ceric ammonium nitrate in 20.0 g methanol and 5.2 g octyl alcohol under argon to maintain anhydrous conditions during the reaction was added 13.1 g of anhydrous 25% w/w sodium methoxide solution. After swirling, the bright yellow slurry was diluted with 25.3 g toluene. The methanol was distilled off while heating until the boiling point reached 104° C. The mixture was filtered, and the solids washed with 5×8 g toluene. The solid was dried in a vacuum overnight to give essentially pure ammonium nitrate, weight 5.0 g (theory 5.1 g).

The filtrate from the reaction mixture was concentrated under reduced pressure to give 6.8 g ceric tetraoctoxide as a dark orange oil (Theory=6.6 g). Ash analysis gave 26.8% ash, carbon 58.4%, hydrogen 10.5% (Theory=26.4%, 58.5%, 10.4%, respectively).

EXAMPLE 4

Preparation of Ceric Tetramethoxide from Ceric Ammonium Nitrate and Sodium Methoxide Sodium methoxide solution (25% w/w, 260.4 g) was added to a stirred solution of ceric ammonium nitrate (109.5 g) in methanol (440.0 g) under argon, to maintain anhydrous conditions during the reaction. The yellow mixture was refluxed for 3 hours. Then, the solvent was removed under reduced pressure, to give a bright yellow solid. This material was transferred to an extraction thimble and refluxed with methanol overnight, to remove sodium nitrate. The residue in the thimble, the ceric tetramethoxide, was then dried under reduced pressure, to give 50.2 g bright yellow ceric tetramethoxide (Theory 52.8 g). The methanol solution was concentrated to dryness to give 103 g of a white solid (Theory 101.8 g), predominantly NaNO₃. Elemental analysis indicated that the product was only slightly hydrolysed. Ash 66.4%, carbon 17.11%, hydrogen 4.2% (Theory 65.1%, 18.2%, 4.6%, respectively).

EXAMPLE 5

Preparation of Ceric Tetra(acetylacetonate) from Ceric Tetramethoxide reaction mixture Ammonia gas (3.9 g, 229 mole) was absorbed by a solution of ceric ammonium nitrate (29.88 g, 0.0502 mole) in 93.90 g methanol. After stirring the bright yellow slurry one hour, acetylacetone (20.5 g, 0.2048 mole) was added dropwise over 0.5 hour to give a black-red solution. The reaction mixture was evaporated to dryness under vacuum, and then the solid was suspended in methylene chloride (87.8 g). The salts were filtered off as white needles (22.13 g, 0.06% ash) after washing. The dark red filtrate was evaporated to dryness under reduced pressure to give 30.09 g dark maroon powder of ceric (acetylacetonate) containing some residual ammonium nitrate. Elemental analysis after correcting for the ammonium nitrate indicated 33.05% ash, 45.64% C, and 5.3% H (Theory 32.08%, 44.77% and 5.26%, respectively).

EXAMPLE 6

Preparation of Ceric Tetraoleyloxide in a slight excess of Oleyl Alcohol from Ceric Ammonium Nitrate in Methanol and Ammonia Ammonia gas (2.8 g, 0.1644 mole) was absorbed in one hour by a solution of ceric ammonium nitrate (16.77 g, 0.0300 mole) in oleyl alcohol (38.04 g) and methanol (74.77 g). The excess of methanol and ammonia was distilled from the dull orange slurry to give a thick orange paste, containing ceric tetra(oleyloxide) and ammonium nitrate. Hexane (90.2 g) was added to the paste to dissolve the ceric tetra(oleyloxide), then ammonium nitrate (14.75 g, theory 14.41 g) also containing some cerium tetra(oleyloxide) was filtered off and washed with fresh hexane. The filtrate was concentrated down to a deep yellow-orange oil, 43.87 g (theory=42.12 g), analysis, 7.3% ash.

EXAMPLE 7

Preparation of Ceric Tetramethoxide from Ceric Ammonium Nitrate, Ammonia, and Methanol Anhydrous ammonia gas (24.7 g) was added very slowly above the surface to a solution of ceric ammonium nitrate (16.45 g) in methanol (300 g) with vigorous stirring over 5 hours. The solids were filtered off, and washed four times with methanol. The residue after drying was 10.1 g of bright yellow solid, ceric tetramethoxide. The ceric methoxide was an association complex with methanol, due to the larger amount of methanol, and exhibited a much greater stability to hydrolytic decomposition, as compared to the product made in Example 2. Elemental analysis gave ash 57.2%, carbon 18.7% and hydrogen 5.37% (Theory 65.1%, 18.2%, 4.6%, respectively).

The methanol filtrate was evaporated to dryness, to give the theoretical amount, 14.28 g, of ammonium nitrate.

Having regard to the foregoing disclosure the following is claimed as inventive and patentable embodiments thereof:

1. A process for preparing ceric alkoxides which comprises reacting ceric ammonium nitrate with an alcohol under anhydrous conditions in the presence of an anhydrous base at a temperature within the range from about −30° C. to about 200° C. until ceric alkoxide and the nitrate salt of the base are formed.

2. A process according to claim 1 in which the alcohol is a lower aliphatic alcohol having from one to five carbon atoms.

3. A process according to claim 1 in which the alcohol is a higher aliphatic alcohol having at least six up to about twenty carbon atoms.

4. A process according to claim 1 in which the alcohol is a cycloaliphatic alcohol having from three to about twenty carbon atoms.

5. A process according to claim 1 in which the alcohol is an alkyl aromatic alcohol having from seven to about twenty carbon atoms.

6. A process according to claim 1 in which the alcohol is selected from the group consisting of higher aliphatic alcohols having at least six up to about twenty carbon atoms; cycloaliphatic atoms having from three to about twenty carbon atoms; alkyl aromatic alcohols having from seven to about twenty carbon atoms; and is incorporated directly in the reaction mixture together with a lower aliphatic alcohol having from one to five carbon atoms.

7. A process for preparing ceric alkoxides of a higher alcohol selected from the group consisting of higher aliphatic alcohols, having at least six up to about twenty carbon atoms; cycloaliphatic alcohols having from three to about twenty carbon atoms and alkyl aromatic alcohols having from seven to about twenty carbon atoms, which comprises transetherifying ceric alkoxide of a lower aliphatic alcohol having from one to about five carbon atoms with the higher alcohol under anhydrous conditions in the presence of anhydrous base.

8. A process according to claim 7, which comprises distilling off free lower aliphatic alcohol in the course of the transetherification, to drive the transetherification towards completion.

9. A process according to claim 7, carried out while separating by distillation any free alcohol formed in the course of the reaction.

10. A process according to claim 1, carried out in solution in an inert solvent in which ceric ammonium nitrate is soluble.

11. A process according to claim 10, in which the solvent is the alcohol of which the alkoxide is to be formed.

12. A process according to claim 1, in which the anhydrous base is ammonia or an alkali metal alkoxide.

13. A process according to claim 12 in which the anhydrous base is an alkali metal alkoxide of the alcohol of the cerium alkoxide.

14. A process according to claim 1 carried out at a reaction temperature within the range from room temperature up to about 250° C.

15. A process according to claim 1, in which the cerium alkoxide reaction product is recovered and separated from the nitrate salt by extraction with a solvent for one of the alkoxide and the nitrate salt.

* * * * *